United States Patent [19]

Yilma et al.

[11] Patent Number: 5,718,902
[45] Date of Patent: Feb. 17, 1998

[54] DOUBLE RECOMBINANT VACCINIA VIRUS VACCINES

[75] Inventors: Tilahun D. Yilma; Luis D. Giavedoni, both of Davis, Calif.

[73] Assignee: The Regents of the University of California, Oakland, Calif.

[21] Appl. No.: 716,590

[22] Filed: Jun. 17, 1991

[51] Int. Cl.$^6$ .................. A61K 39/155; A61K 39/00; C12N 15/00; C07H 21/02

[52] U.S. Cl. .................. 424/211.1; 424/184.1; 424/192.1; 435/172.1; 435/948; 536/23.1

[58] Field of Search .................. 424/89; 536/27; 435/948, 172.1

[56] References Cited

U.S. PATENT DOCUMENTS 4,722,848  2/1988  Paoletti et al. .................. 424/89

OTHER PUBLICATIONS

Yilma et al. (1988) Science 242:1058–1061.
Yilma (1990) Biotechnology 8:1007–1009.
Perkus et al. (1985) Science 229:981.
Buller et al. (1985) Nature 317:813.

*Primary Examiner*—Lynette F. Smith
*Attorney, Agent, or Firm*—Townsend and Townsend and Crew LLP

[57] ABSTRACT

Vaccines comprising a recombinant vaccinia virus expressing at least two heterologous genes encoding pathogen antigens are described. A first antigen gene is inserted into the thymidine kinase gene of the vaccinia virus and a second antigen gene is inserted into the hemagglutinin gene of the vaccinia virus. In particular, the hemagglutinin and fusion genes of the rinderpest virus have been inserted into the thymidine kinase and hemagglutinin genes of the vaccinia virus, respectively. Such double recombinant viruses have been found to be highly attenuated while remaining effective in protecting an inoculated host.

14 Claims, 4 Drawing Sheets

DOUBLE RECOMBINANT VACCINIA VIRUS VACCINES

BACKGROUND OF THE INVENTION

1. Field of the Invention

The present invention relates generally to the field of vaccine preparation and use. More particularly, the present invention relates to recombinant vaccinia virus vaccines capable of expressing antigens from other pathogens.

Vaccinia virus is a poxvirus capable of infecting a variety of animal hosts including rabbits, goats, camels, sheep, and cattle. Because of its antigenic similarity to the variola (smallpox) virus, live vaccinia has proven successful in immunizing individuals against smallpox infection. Indeed, the name vaccine was originally derived from the name vaccinia.

Recently, there has been widespread interest in the use of recombinant vaccinia virus for vaccination against a variety of viral and other infectious diseases. Vaccinia is a very large virus having a genome of about 187 kb. About 10% or greater of the genome is either redundant or encodes functions which are not essential for replication. The insertion of heterologous genes into such non-essential regions promises to provide novel vaccines for numerous diseases. For example, an influenza vaccine has been developed by inserting the influenza hemagglutinin gene into the vaccinia virus thymidine kinase gene. The resulting recombinant vaccinia virus was then used as an immunogen in a vaccine for protection against influenza. Other examples of successful recombinant vaccinia virus vaccines have also been reported.

Of particular interest to the present invention, recombinant vaccinia virus vaccines have been developed to immunize against infection by the rinderpest virus. Rinderpest is a highly contagious viral disease of cattle, buffalo, and other ruminants, and is characterized by high fever, perfuse bloody diarrhea, 100% morbidity, and greater than 95% mortality. The rinderpest virus is a member of the family Paramyxoviridae and the genus Morbilliviruses. The recombinant vaccines relied on inserting either the hemagglutinin or the fusion gene of the rinderpest virus into the thymidine kinase gene of vaccinia. Cattle vaccinated with either recombinant were protected when subsequently challenged with lethal doses of rinderpest virus, but certain of the cattle had significant anamenstic response after challenge, indicating replication of the challenge virus. No anamenstic response, however, occurred in cattle vaccinated with a cocktail of both recombinants. The use of such a cocktail vaccine in the field, however, is cumbersome and expensive and particularly inappropriate in less developed countries where rinderpest is a problem.

Vaccines based on vaccinia virus suffer from safety problems as a result of the formation of pock lesions at the site of inoculation. The pock lesions can be a source of accidental contamination of the vaccinia virus. In particular, if the lesion is accidentally opened or otherwise compromised, the replicating virus can be released to the environment where it can infect unintended hosts. Moreover, even highly attenuated vaccinia virus strains can be harmful to immunocompromised individuals, such as patients suffering from acquired immunodeficiency syndrome (AIDS).

For these reasons, it would be desirable to provide improved recombinant vaccinia virus vaccines capable of eliciting immunity against a variety of viral and other pathogens. It would be particularly desirable if the vaccinia virus vaccines were able to provide immunity against subsequent challenge with even very lethal doses of the pathogen while the recombinant vaccinia virus itself is highly attenuated so that it will produce minimal or no pock formation. Moreover, it would be desirable to provide recombinant vaccinia virus vaccines capable of expressing two or more antigenic genes from the same or different pathogens. In particular, it would be desirable to provide improved vaccines against rinderpest infection which are capable of affording a high degree of immunity with only a single recombinant vaccinia virus strain.

2. Description of the Background Art

Vaccines against rinderpest virus based on recombinant vaccinia virus expressing either the hemagglutinin or the fusion gene of rinderpest are reported in Yilma et al. (1988) Science 242: 1058–1061 and Yilma (1990) Biotechnology 8:1007–1009. The latter reference states that the authors "plan to use the cocktail of both the H [hemagglutinin] and F [fusion] recombinants, or a single recombinant expressing both genes, which [the authors] have very recently developed." (page 1008). Perkus et al. (1985) Science 229:981 have prepared a polyvalent recombinant vaccinia virus expressing herpes simplex virus, hepatitis B virus, and influenza virus antigens. While inoculation of rabbits was found to induce a humoral response, no protection against subsequent challenge was demonstrated. Insertional inactivation of the thymidine kinase gene has been shown to further attenuate the Wyeth strain of vaccinia virus (Buller et al. (1985) Nature 317:813). The preparation of recombinant vaccinia virus vaccines is described generally in U.S. Pat. No. 4,722,848, the disclosure of which is incorporated herein by reference.

SUMMARY OF THE INVENTION

Vaccines conferring immunity against vital and other pathogens comprise recombinant vaccinia virus having both the thymidine kinase and hemagglutinin genes inactivated, with at least one of said genes being inactivated by insertion of a heterologous gene encoding an exogenous antigen of a pathogen. Usually, the recombinant vaccinia virus will have a first gene encoding a first antigen inserted into the thymidine kinase gene and a second gene encoding a second antigen inserted into the hemagglutinin gene. Surprisingly, it has been found that such double recombinant vaccinia virus vaccines are capable of conferring a strong protective immunity against the pathogen while being sufficiently attenuated to produce little or no pock lesion. Thus, the vaccines are effective while remaining very safe and unlikely to provide a source for release of the recombinant virus and accidential infection.

The first and second antigen genes will normally be from the same pathogen, but may be from different pathogens. The recombinant vaccinia virus may also express additional heterologous antigen gene(s) from either the same or different pathogens. The present invention requires only that both the thymidine kinase gene and the hemagglutinin gene be inactivated, with at least one of the genes being insertionally inactivated with a heterologous antigen gene.

In a preferred embodiment, the vaccine is a rinderpest vaccine comprising vaccinia virus expressing the hemagglutinin and fusion genes of the rinderpest virus. In a particularly preferred embodiment, the hemagglutinin and fusion genes are inserted into the thymidine kinase and hemagglutinin genes of the vaccinia virus, respectively.

In a first method according to the present invention, a susceptible host is inoculated with a recombinant vaccinia virus to confer immunity against a viral or other pathogen.

The vaccinia virus expresses a first heterologous gene encoding a first antigen of a pathogen inserted into the thymidine kinase gene and a second heterologous gene encoding a second antigen of a pathogen inserting into the hemagglutinin gene.

In a second method according to the present invention, a recombinant vaccinia virus is produced by inserting a first heterologous gene encoding a first viral or other antigen into the thymidine kinase gene and a second heterologous gene encoding a second vital or other antigen into the hemagglutinin gene of the vaccinia virus. The recombinant virus is propagated to produce virus suitable for incorporation into vaccine compositions. Preferably, the vaccinia virus is an attenuated strain, more preferably being the Wyeth strain.

DESCRIPTION OF THE SPECIFIC EMBODIMENTS

Figure 1:
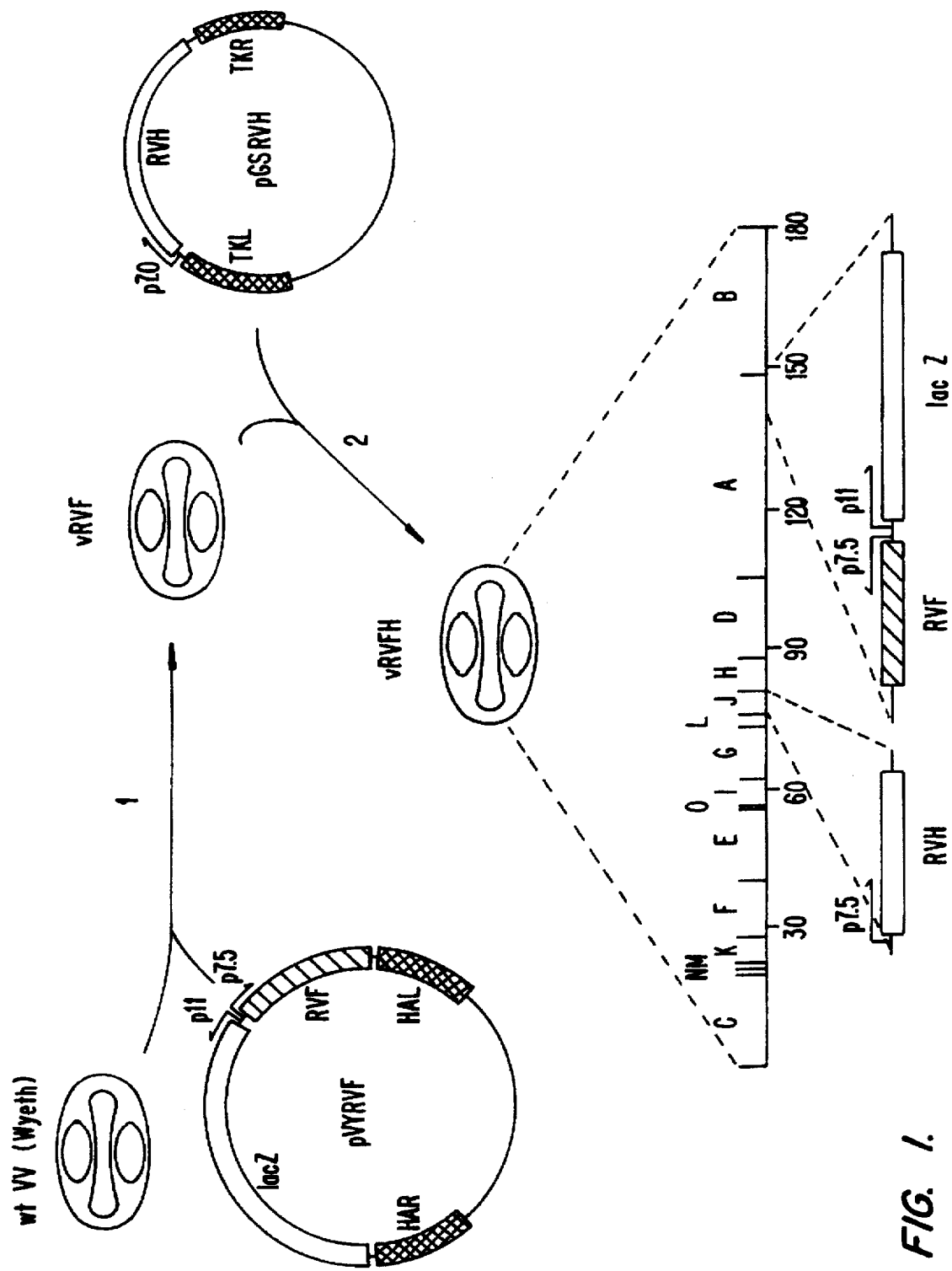
FIG. 1 illustrates the construction of a vaccinia virus double recombinant strain expressing both the fusion and hemagglutinin genes of the rinderpest virus, as described in more detail in the Experimental section hereinafter.

According to the present invention, vaccines are provided for conferring immunity against infection by a variety of pathogens, particularly viral pathogens, but also bacteria, spirochetes, protozoa, and the like. The vaccines comprise a recombinant vaccinia virus expressing at least one heterologous gene from at least one pathogen, wherein both the thymidine kinase and hemagglutinin genes of the vaccinia virus have been inactivated. At least one of the genes will have been inactivated by insertion of the heterologous gene and usually both genes will have been insertionally inactivated, either with the same or different heterologous genes expressing antigens from the same or different pathogens.

The heterologous genes encode exogenous antigens of the pathogen which are capable of eliciting a virus neutralizing (humoral and/or cell-mediated) response when administered to a susceptible host. By exogenous, it is meant that the genes expressing the antigens are not native to the vaccinia strain which is recombinantly modified. Usually, the vaccinia virus will express at least two antigens from a single pathogen, more usually expressing at least two different antigens from the same pathogen. Optionally, the vaccinia virus may express three or more antigens. A list of pathogens with corresponding antigens is provided in Table 1.

TABLE 1

| Pathogen | Antigen(s) | Reference |
|---|---|---|
| Rinderpest virus | Hemagglutinin Fusion | Yilma et al. (1988) Science 242:1058–1061. |
| Hepatitis B virus | Surface Antigen | Smith et al. (1983) Nature 302:490. |
| Influenza virus | Hemagglutinin (HA) PB1 PB2 PA NP M1 NS1 | Panicali et al. (1983) PNAS U.S.A. 80:5364; Flexner et al. (1988) Nature 335:229; Yewdell et al. (1985) PNAS U.S.A. 82:19; Smith et al. (1987) Virol. 160:336; Smith et al. (1983) PNAS U.S.A. 80:7155; Coupar et al. (1986) J. Immunol. 16:1479; and Townsend et al. (1988) J. Exp. Med. 168:1211. |
| Herpes simplex virus | Glycoprotein D (gD) Thymidine kinase (TK) Glycoprotein B Glycoprotein G | Paoletti et al. (1984) PNAS U.S.A. 81:193; Panicali et al. (1982) PNAS U.S.A. 79:4927; and McLaughlin-Taylor et al. (1988) J. Gen. Virol. 62:1731; and Sullivan and Smith (1989) J. Gen. Virol. 68:2587. |
| Plasmodium knowlesi | Sporozoite | Smith et al. (1984) Science 224:397. |
| Vesicular stomatitis virus | G protein N protein M protein | Mackett et al. (1985) Science 227:433; and Li et al. (1988) J. Virol. 62:776. |
| Human immunodeficiency virus | gp160 gag/pol gene products | Chakrabarti et al. (1986) Nature 320:535; and Flexner et al. (1988) J. Virol. 166:339. |
| Human papilloma virus | L1 gene product | Browne et al. (1988) J. Gen. Virol. 69:1263. |
| Human cytomegalovirus | Glycoprotein B | Cranage et al. (1986) EMBO J. 5:3057. |
| Epstein-Barr virus | gp340/220 | Mackett et al. (1985) EMBO. J. 4:3229; and Morgan et al. (1988) J. Med. Virol. 25:189. |
| Psuedorabies | gp50 | Marchioli et al. (1987) J. Virol. 61:3977. |
| Measles virus | Hemagglutinin fusion | Drillien et al. (1988) PNAS U.S.A. 85:1252. |
| Plasmodium flaciparum | CSP S-antigen | Langford et al. (1986) Mol. |

TABLE 1-continued

| Pathogen | Antigen(s) | Reference |
|---|---|---|
| | | Cell Biol. 6:3191. |

In a preferred embodiment, first and second heterologous genes encoding the desired antigens will be inserted into the thymidine kinase and hemagglutinin genes of the vaccinia virus, respectively. It has been found that the resulting inactivation of both the thymidine kinase and hemagglutinin genes results in substantial attenuation of the vaccinia virus without significant loss of the ability of the virus to elicit virus neutralizing antibodies and protect an inoculated host against subsequent challenge. The location of the thymidine kinase gene and the hemagglutinin gene on the vaccinia virus genome is illustrated in FIG. 1 which depicts a HindIII digest of the vaccinia virus genome (Wyeth strain), wherein thymidine kinase is in the J region and hemagglutinin is in the A region. The thymidine kinase gene is further described in Buller et al. (1985) Nature 317:813–815 and the hemagglutinin gene in Shida (1986) Virology 150:451–462. Both of these references are incorporated herein by reference.

Genes encoding for the desired antigens can be isolated from the pathogens using conventional techniques. In the case of RNA viruses, cDNA copies of the genes can be made.

Suitable vectors for inserting the antigen genes into the thymidine kinase and hemagglutinin genes of vaccinia virus are described in the scientific literature. A particularly suitable vector for inserting antigen genes into the thymidine kinase gene of vaccinia is pGS53 described in Mackett et al. (1985) Science 227:433–435, while a vector for inserting antigen genes into the hemagglutinin gene of vaccinia is pVY6 described in Flexner et al. (1988) Nature 335:259–262. The disclosures of both of these references are incorporated herein by reference. Incorporation of genetic material into these vectors and the use of these vectors for inserting the genetic material into vaccinia virus is well within the skill of the art. Standard procedures for constructing vaccinia virus recombinants are described in Chakrabarti et al. (1985) Mol. Cell Biol. 5:3403 and U.S. Pat. No. 4,722,848, the disclosures of which are incorporated herein by reference.

The vaccinia virus which is modified by insertion of the antigen genes will preferably be an attenuated strain, i.e., having reduced virulence compared with wild type vaccinia virus. Suitable attenuated vaccinia virus strains include Wyeth (New York City Board of Health), Lister, and the like. Particularly preferred is the use of the Wyeth strain, available from Flow Laboratories, McLean, Va.

The construction of an exemplary double recombinant vaccinia virus expressing the hemagglutinin and fusion genes of the rindepest virus is described in detail in the Experimental section hereinafter. The hemagglutinin and fusion genes of rinderpest are inserted into the thymidine kinase and hemagglutinin genes of the Wyeth (NYCBH) strain of vaccinia virus, respectively. The resulting double recombinant virus was found to be highly attenuated and in particular was found to cause little or no pock lesion formation when inoculated into cattle and other hosts. The double recombinant virus, however, was found to be a very effective vaccine and provided protection of cattle against highly lethal doses of the rinderpest virus. It is believed that the exemplary double recombinant vaccinia virus will also afford protection against other Morbilliviruses which are antigenically similar to rinderpest, including the peste-despetits ruminants (PPR) virus, the measles virus, the canine distemper virus, and the Morbillivirus of seals.

The recombinant vaccinia virus may be propagated in cell culture or by scarification of susceptible hosts, such as calves, sheep, or horse, and the like. Methods for isolating and purifying the virus produced from both cell culture and animal sources are well known in the art.

Vaccine compositions according to the present invention will incorporate the live attenuated double recombinant vaccinia viruses prepared as described above. The vaccinia virus may be incorporated in a physiologically-acceptable medium, such as water, saline, phosphate buffered saline, and may be administered in any conventional manner, including subcutaneously, intradermally, orally, or nasally, and the like. The preparation and administration of such vaccine compositions are described in numerous standard references, such as Remington's Pharmaceutical Sciences, Mack Publishing Company, Easton, Pa., 16th Ed., 1982, the disclosure of which is incorporated herein by reference. The preparation of veterinary vaccines is described in Tizard, An Introduction to Veterinary Immunology, 2nd. Ed., 1982, the disclosure of which is incorporated herein by reference.

In veterinary applications, the vaccines of the present invention may frequently be lyophilized and administered by scarification. Scarification procedures are well known in the art and described in standard references, such as Quinnan, ed., Vaccinia Virus as Vector for Vaccine Antigens, Elsevier-North Holland, 1985, the relevant disclosure of which is incorporated herein by reference.

The dosage form and virus content of the vaccine will vary depending on the nature of the host and the disease. For injectable vaccines, a single dose will usually have a total volume including carrier, and any other components, in the range from about 0.05 ml to about 0.1 ml. The amount of virus in each dose will usually be in the range from about $10^2$ to $10^8$ pfu.

The number and temporal spacings of the inoculations will be sufficient to elicit the desired immunoprotective response against subsequent challenge by the pathogen or pathogens. There will be at least one inoculation, and in many cases at least two inoculations spaced at least one month apart. In many cases, a final inoculation may be administered at some longer interval following initial series of administrations. The selection of optimum administration patterns for a particular vaccine formulation is well within the skill of the art.

The following examples are offered by way of illustration, not by way of limitation.

EXPERIMENTAL

Materials and Methods

Cells and Viruses

Vero, human 143 TK$^-$, and CV-1 cells were propagated in Dulbecco's modified Eagle's medium (DMEM) supplemented with heat-inactivated fetal bovine serum. For the propagation of TK$^-$ cells, DMEM was supplemented with 5-bromodeoxyuridine (BrdUrd) at 25 ug/ml. The highly pathogenic Kabete "O" strain of rinderpest virus (RPV) was propagated in Vero cells and used in all studies. The Wyeth strain of vaccinia virus (VV; clone B-3-1), obtained from Flow Laboratories (McLean, Va.) was used exclusively for the generation of recombinants. All VV recombinants were propagated in Vero cells according to the guidelines of the Animal and Plant Health Inspection Service of the United States Department of Agriculture (USDA-APHIS) and the Office Internationale de Epizooties (OIE).

Recombinant Plasmids

Full-length cDNAs coding for the hemaggltuinin (H) and fusion (F) proteins of RPV were cloned as described previously (Yamanaka et al. (1988) Virology 166:251-253 and Hsu et al. (1988) Virology 166:149-153). Plasmid vectors pVY6 (Flexner et al. (1988) Nature 335:259-262) and pGS53 (Mackett et al. (1985) Science 227:433-435) were utilized for the construction of vRVFH, the vaccinia virus double recombinant expressing both the F and the H genes of RPV. Plasmid vectors pVY6 and pGS53 direct the cloning of genes in the hemaggltuinin (HA) and thymidine kinase (TK) regions of the vaccinia virus genome, respectively.

Radioimmunoprecipitation

Proteins expressed by VV recombinants were characterized by radioimmunoprecipitation as previously described (Grubman et al. (1988) Virology 163:261-267). Rabbit anti-measles H was used for specific immunoprecipitation of the H protein of RPV. Rabbit antiserum directed against the carboxy terminus of measles virus F protein was used for the immunoprecipitation of the F protein of RPV. Except for the first amino acid, the 18 amino acid long peptide used for generation of the antisera was completely conserved between measles virus and RPV (Vialard et al. (1990) J. Virol. 64:37-50 and Hsu et al. (1988), supra.).

Immunization Studies in Cattle

Protective immune response studies were conducted in yearling cattle in the high containment facility at the Plum Island Animal Disease Center (USDA-APHIS) according to proper institutional guidelines. Cattle used in these experiments were shown to be seronegative to RPV and vaccinia virus by serum neutralization (SN) and plaque reduction assays, respectively. One contact animal (#111), however, had cross-reacting antibody to RPV which was not protective (Table 2). Cattle were vaccinated with $10^8$ pfu of VV recombinants by intradermal inoculation and scarification in the neck region. In addition, contact animals were housed with vaccinates in order to test for transmission of VV recombinants from vaccinated to nonvaccinated groups of animals. On the day of challenge, one additional cow was brought in as a fresh control to assure the presence of an animal susceptible to RPV, in case of VV recombinants had been transmitted to contact animals. For the determination of protective immunity, all cattle were challenged with $10^3$ TCID$_{50}$ of RPV one month postvaccination (Yilma et al. (1988) Science 242:1058-1061). It has been demonstrated previously in a study using 19 animals, that as little as one TCID$_{50}$ administered subcutaneously in the prescapular lymph node region induced clinical rinderpest with 100% mortality (Yilma et al. (1988), supra.).

RESULTS

Construction of VV Recombinants

The strategy for the construction of vRVFH, the vaccinia virus double recombinant expressing both the F and H genes of RPV, is outlined in FIG. 1. First, vRVF, the single recombinant expressing the F gene from the HA region of the vaccinia virus genome, was constructed. Briefly, the F cDNA of RPV was excised from plasmid pvRVF6 (Yilma et al. (1988) supra.) by digestion with EcoR1, filled in with the Klenow polymerase, and then cloned in the SmaI site of plasmid vector pVY6 to generate pVYRVF. The F gene was then cloned in the HA region of vaccinia virus by homologous recombination between pVYRVF and the Wyeth strain of vaccinia virus in CV-1 cells. Recombinants expressing the F gene (vRVF) were selected by their blue phenotype in the presence of X-gal. In preparation for the construction of vRVFH (double recombinant), the H gene of RPV was excised from plasmid pRVH6 by digestion with EcoR1 (Yilma et al. (1988) supra.). The fragment was then blunted with Klenow polymerase and cloned in the SmaI site of the vaccinia virus shuttle vector pGS53 to generate pGSRVH. The double recombinant (vRVFH) was generated by homologous recombination between pGSRVH and vRVF in CV-1 cells (Mackett et al. (1985), supra.). TK$^-$ vaccinia viruses were picked by BrdUrd selection, and double recombinants were distinguished from contaminating, spontaneous TK$^-$ mutants by plaque hybridization with H cDNA of RPV.

Expression of F and H Proteins of RPV by VV Recombinants

Figure 2:
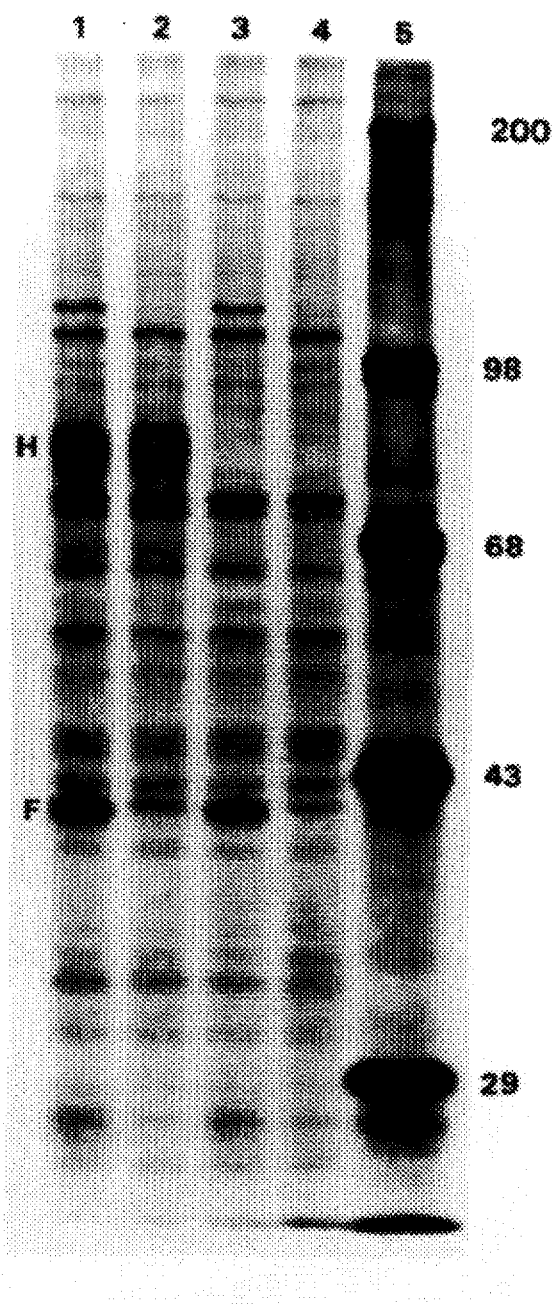
FIG. 2 is a polyacrylamide gel characterizing the polypeptides expressed by the vaccinia virus double recombinant strain produced in the Experimental section hereinafter.

The expression of authentic F and H proteins by vRVFH, F by vRVF, and H by vRVH was demonstrated by specific immunoprecipitation (FIG. 2). Monolayers of human 143 TK$^-$ cells were infected with 10 pfu/cell of vaccinia virus in medium containing no methionine or cysteine. After 2 h at 37°, 100 μCi of [$^{35}$S]methionine+cysteine (translable, Amersham) was added and the incubation was continued for overnight (16 h). A mixture of anti-F and anti-H antibodies to measles virus was used to precipitate polypeptides from infected cells. The preparation of cytoplasmic extracts, immunoprecipitation, and polyacrylamide gel electrophoresis were performed as previously described (Varsanyi et al. (1987) J. Virol. 61:3896). Lane 1: Cells infected with vaccinia virus double recombinant (vRVFH) expressing both the F and H genes of RPV. Lane 2: Cells infected with vaccinia virus single recombinant (vRVF) expressing the F gene of RPV. Lane 3: Cells infected with vaccinia virus single recombinant (vRVH) expressing the H gene of RPV. Lane 4: Wild type vaccinia virus (Wyeth). Lane 5: Molecular weight markers (kDa). Fluorographs revealed that cells infected with vRVFH expressed both the F and the H proteins of RPV of the expected size and MW. Similarly, the F protein expressed by vRVF and the H by vRVH were of the correct size suggesting that the extent of glycosylation is similar to that occurring in cells infected with RPV (Grubman et al. (1988), supra.).

Immunization Studies in Cattle

Two groups of cattle were vaccinated with VV recombinants in separate isolation rooms. In the first group, five animals were vaccinated with vRVFH (Table 2).

TABLE 2

SN titers of cattle vaccinated with vaccinia virus double recombinant (vRVFH) expression the F and H genes of RPV.

| Cow # | Day 0 | Day 8 | Day 14 | Day 21 | Day 28 | Day 42 |
|---|---|---|---|---|---|---|
| 102 | — | — | — | — | 1 | Dead |
| 111 | 16 | 12 | 6 | 12 | 6 | Dead |
| 122 | 0 | 0 | 0 | 2 | 6 | Dead |
| 112 | 2 | 64 | 16 | 64 | 48 | 256 |
| 113 | 0 | 32 | 24 | 48 | 24 | 32 |
| 126 | 0 | 128 | 48 | 64 | 24 | <100 |
| 134 | 0 | 48 | 64 | 64 | 96 | 96 |
| 135 | 0 | 12 | 64 | 32 | 64 | 64 |

Cow #102 was a control animal that was included in the group on the day of challenge (day 28). Animals #111 and #122 were unvaccinated, contact controls. The rest of the animals were vaccinated on day 0 with $10^8$ pfu of vRVFH, and serum samples were taken weekly during the course of the experiment. SN titers were determined by the prevention of the cytopathic effects of 100 TCID$_{50}$ of RPV in Vero cells. On day 28, all animals were challenged with 1000 TCID$_{50}$ of the pathogenic strain of Kabete "O" RPV.

In the second group, four animals were vaccinated with a cocktail of vRVF and vRVH (Table 3).

TABLE 3

SN titers of cattle vaccinated with a cocktail of vaccinia virus single recombinants expressing the F (vRVF) and H (vRVH) genes of RPV.

| Cow # | Day 0 | Day 8 | Day 14 | Day 21 | Day 28 | Day 42 |
|-------|-------|-------|--------|--------|--------|--------|
| 121   | 0     | 0     | 0      | 0      | 0      | Dead   |
| 133   | 0     | 3     | 0      | 1      | 0      | Dead   |
| 101   | 0     | 24    | 24     | 96     | 128    | 256    |
| 118   | 0     | 128   | 64     | 24     | 12     | 64     |
| 124   | 0     | 24    | 32     | 64     | 96     | 64     |
| 131   | 0     | 96    | 384    | 32     | 128    | 64     |

Animals #121 and #133 were unvaccinated, contact controls. The rest of the animals were vaccinated on day 0 with $10^8$ pfu of vRVF+vRVH, and serum samples were taken weekly during the course of the experiment. SN titers were determined by the prevention of the cytopathic effects of 100 TCID$_{50}$ of RPV in Vero cells. On day 28, all animals were challenged with 1000 TCID$_{50}$ of the pathogenic strain of Kabete "O" RPV.

In addition, two unvaccinated animals were included in each group in order to assess the transmissibility of VV recombinants from vaccinated to contact animals.

Figure 3A:
FIG. 3A is a photograph of the neck region of a cow inoculated with the double recombinant vaccinia virus strain, as described in detail in the Experimental section hereinafter. No pock lesions are apparent.
Figure 3B:
FIG. 3B is a photograph of vaccinia virus-induced pock lesions in the neck region of a cow inoculated with the cocktail of two single recombinant vaccinia viruses of the same strain, as described in detail in the Experimental section hereinafter.

Pock lesions developed as early as four days in cattle vaccinated with the cocktail (FIG. 3B). The lesions were limited to the site of inoculation and were healed completely by two weeks postvaccination. In contrast, animals vaccinated with vRVFH developed very tiny or no detectable lesions (FIG. 3A). Cow #126 (FIG. 3) was vaccinated with vRVFH (double recombinant); note the lack of detectable pock lesions at the site of inoculations (FIG. 3A). Cow #118 was vaccinated with vRVF+vRVH (Cocktail) and developed pock lesions at the two sites of inoculation (see arrows) (FIG. 3B).

A thorough examination failed to demonstrate pock lesions in the contact animals in both groups. Further, serum samples taken on the days of vaccination (day 0) and challenge (day 28) were negative to vaccinia virus by SN and plaque reduction assays (data not shown). All animals vaccinated with VV recombinants produced SN antibodies to RPV (Tables 2 and 3). One month post vaccination, all animals in both groups were challenged with $10^3$ TCID$_{50}$ of the pathogenic Kabete "O" strain of RPV. Cattle vaccinated with VV recombinants (both groups) were completely protected from rinderpest, exhibiting no detectable illness, and a normal temperature of 38° C. The four unvaccinated contacts (including #111 with the cross-reactive antibody to RPV) and the one control animal developed high fever (42° C.) by day two and died by day six after challenge. They also developed lesions typical of severe rinderpest, characterized by sloughing and erosion of the epithelial lining of the gastrointestinal tract and bloody diarrhea. After daily monitoring for two weeks and a lack of detectable clinical disease in vaccinated animals, the experiment was terminated.

All cattle vaccinated with the recombinants produced SN antibody to RPV as early as 8 days after vaccination. However, all contact and control animals lacked detectable SN antibody to RPV during the course of the experiment.

Although the foregoing invention has been described in detail for purposes of clarity of understanding, it will be obvious that certain modifications may be practiced within the scope of the appended claims.

What is claimed is:

1. A vaccine for conferring immunity against rinderpest virus, said vaccine comprising recombinant vaccinia virus expressing the fusion and hemagglutinin genes of rinderpest, wherein at least the thymidine kinase gene and the hemagglutinin gene of the vaccinia virus have been inactivated and wherein the vaccinia virus is attenuated so as to produce very tiny or no pock formation.

2. A vaccine as in claim 1, wherein the hemagglutinin and fusion genes of rinderpest virus have been inserted into the thymidine kinase and hemagglutinin genes of vaccinia virus, respectively.

3. A vaccine as in claim 1, wherein the recombinant vaccinia virus is present in an physiologically acceptable carrier in an amount effective to elicit viral neutralizing activity against the pathogen when administered to a susceptible host.

4. A vaccine as in claim 1, which has been lyophilized.

5. A vaccine as in claim 1, wherein the recombinant virus is derived from an attenuated strain of vaccinia.

6. A vaccine as in claim 5, wherein the attenuated strain is Wyeth.

7. A method for vaccinating a susceptible host to confer immunity against, rinderpest virus, said method comprising inoculating the host with a recombinant vaccinia virus having both the thymidine kinase gene and the hemagglutinin inactivated and a hemagglutinin gene of rinderpest virus inserted into the thymidine kinase gene and the fusion gene of rinderpest virus inserted into the hemagglutinin gene, wherein the vaccinia virus is attenuated so as to produce very tiny or no pock formation.

8. A method as in claim 7, wherein the recombinant vaccinia virus is present in a physiologically acceptable carrier in an amount effective to elicit viral neutralizing activity against the pathogen when administered to a susceptible host.

9. A method as in claim 7, wherein the recombinant vaccinia virus has been lyophilized.

10. A method as in claim 7, wherein the recombinant virus is derived from an attenuated strain of vaccinia.

11. A method as in claim 10, wherein the attenuated strain is Wyeth.

12. A method for producing a recombinant vaccinia virus suitable for use as a vaccine against rinderpest disease, said method comprising:

inserting a hemagglutinin gene of rinderpest virus into the thymidine kinase gene of a vaccinia virus;

inserting a fusion gene of rinderpest virus into the hemagglutinin gene of the vaccinia virus; and propagating the resulting recombinant virus, wherein the vaccinia virus is attenuated so as to produce minimal or no pock formation.

13. A method as in claim 12, wherein the vaccinia virus is an attenuated strain.

14. A method as in claim 13, wherein the attenuated strain is Wyeth.

* * * * *